United States Patent [19]

O'Neill et al.

[11] Patent Number: 4,736,059
[45] Date of Patent: Apr. 5, 1988

[54] PROCESS FOR THE PREPARATION OF MESO 2,5-DIHALOADIPATES

[75] Inventors: Brian T. O'Neill, Westbrook; Harry A. Watson, Jr., Groton, both of Conn.

[73] Assignee: Pfizer Inc., New York, N.Y.

[21] Appl. No.: 82,703

[22] Filed: Aug. 7, 1987

[51] Int. Cl.$^4$ .................. C07C 67/14; C07C 67/52
[52] U.S. Cl. ................... 560/192; 560/191; 562/593; 562/596
[58] Field of Search ............. 560/191, 192; 562/593, 562/596

[56] References Cited

U.S. PATENT DOCUMENTS 3,947,445  3/1976  Henry et al. .................. 260/268

OTHER PUBLICATIONS

Cignarella et al., J. Org. Chem. 26, 1500–1504 (1961).
Le Sueur, J.C.S., vol. 95, pp. 273–279, (1909).
Willstatter et al., Chem Ber, 35, 2065–2073, (1902).
Ingold, J. Chem. Soc. 951–970, (1921).
Blackman & Baltzly, J. Org. Chem., 26, 2750–2755, (1961).
Sturm & Henry, J. Med. Chem. 17, 481–487, (1974).
Lowe et al., J. C. S., Perkin I, 2024–2029, (1973).
Ito et al, Tetrahedron Let., 4643–4646, (1985).
Kurihara et al., Tetrahedron Let., 5831–5834, (1985).
Buckman et al., J. Amer. Chem. Soc. 64., 2696–2700, (1942).

*Primary Examiner*—Werren B. Lone
*Assistant Examiner*—Vera C. Clarke
*Attorney, Agent, or Firm*—Peter C. Richardson; Lawrence C. Akers; Robert F. Sheyka

[57] ABSTRACT

The present process produces the meso dialkyl 2,5-dihaloadipate from a mixture of the racemic dialkyl 2,5-dihaloadipate and meso 2,5-dihaloadipate. In the disclosed process, a 2,5-dihaloadipoyl halide is formed under conditions which result in the formation of an acidic compound. The 2,5-dihaloadipoyl halide is then esterified under conditions wherein the ester of the dihaloadipoyl halide is allowed to remain in contact with the acidic compound, thus allowing the racemic diester to epimerize in the presence of the acidic compound to the meso form and then the meso diester spontaneously crystallizes. In the last stage, the meso diester produced is removed.

9 Claims, No Drawings

PROCESS FOR THE PREPARATION OF MESO 2,5-DIHALOADIPATES

BACKGROUND OF THE INVENTION

Dihaloadipates are important intermediates in the formation of many compounds having pharmaceutical, herbicidal and other attributes. In particular, the esterified derivatives of meso-2,5-dihaloadipates are useful intermediates in the synthesis of heterocycles such as disubstituted pyrrolidines and diazabicyclooctanes.

A number of methods directed to the synthesis of the meso compounds have been reported.

For instance, an article by Willstatter appearing in Chem. Ber., 35, 2065, 1902 reports the synthesis of the diethylester of meso dibromoadipate with very little experimental detail.

In later articles appearing in J. Chem. Soc., 273, 1909 and J. Chem. Soc. 951, 1921, the bromination of the adipoyl halide and latter esterification to yield the diethyl ester resulted in yields of the desired product of 28% and 40%, respectively. The above two references disclose the improved formation of the meso-ester only after high temperature vacuum distillation.

An analogous process affording a 60% yield of the methyl ester of the dihalo adipoyl halide is reported in J. Org. Chem., 26, 2750, 1961. The method reported in this reference also required careful fractionation.

An article appearing in J. Amer. Chem. Soc. 64, 2696, (1942), discloses the preparation of meso methyl dibromoadipate in a 70% yield by (a) a first crop crystallization of 50% of pure meso and (b) fractional distillation of the resulting mother liquor to obtain the remaining 20% of the pure meso compound. These authors report that the diethyl ester was obtained in an overall yield of 46%.

Thus, there remains a need for a process affording the pure meso-2,5-dibromoadipate without resort to careful fractionation or long reaction times.

SUMMARY OF THE INVENTION

The present invention is directed to a process for the preparation of the meso dialkyl 2,5-dihaloadipate from a mixture of racemic dialkyl 2,5-dihaloadipate and meso dialkyl 2,5-dihaloadipate comprising
  (a) halogenating an adipoyl halide under conditions wherein a mixture of racemic and meso-dihalo adipoyl halides are formed, said conditions also resulting in the formation of an acidic compound,
  (b) esterifying said mixture of resultant dihalo adipoyl halides under conditions resulting in the formation of a mixture of racemic dialkyl 2,5-dihaloadipate and meso dialkyl 2,5-dihaloadipate, said conditions also resulting in the formation of an acidic compound,
  (c) allowing the mixture of (b) to remain in contact with the acidic compound produced in steps (a) and (b) for a sufficient period of time to allow spontaneous crystallization of said meso diester, said acidic compound serving to epimerize said racemic dialkyl 2,5-dihaloadipate to said meso dialkyl, 2,5-dihaloadipate,
  (d) removing the meso dialkyl 2,5-dihaloadipate thus produced from the equilibrium mixture of (c) by crystallization, whereby said crystallization of the meso dialkyl 2,5-dihaloadipate drives the equilibrium of the mixture towards formation of the meso dialkyl 2,5-dihaloadipate.

Preferred dialkyl 2,5-dihaloadipates which can be produced by the above process are $C_1$-$C_3$ alkyl diesters, with especially preferred alkyl diesters being the dimethyl and diethyl esters.

Another preferred diester which can be produced by the above process is the dibenzyl ester.

Preferred acidic compounds which epimerize the mixture of the racemic dialkyl 2,5-dihaloadipate and meso dialkyl 2,5-dihaloadipate are hydrogen bromide and hydrogen chloride.

A preferred adipoyl halide which is halogenated in step (a) is adipoyl chloride with a preferred halogenation being the bromination of the adipoyl chloride to produce a dibromoadipoyl halide.

An especially preferred compound produced by the process of the present invention is meso diethyl 2,5-dibromoadipate.

DETAILED DESCRIPTION OF THE INVENTION

The adipoyl halides which are halogenated in step (a) of the present invention are items of commerce and may be obtained from a variety of sources, for example, Aldrich Chemical Company.

The halogenation reaction is conducted at a temperature of from about 70° C. to about 100° C., preferably about 75° C. to about 85° C., with one method being to heat the adipoyl halide to this temperature and then add the halogen to the heated adipoyl halide in the presence of light. The adipoyl halide can be adipoyl chloride, adipoyl fluoride, adipoyl bromide or adipoyl iodide with an especially preferred adipoyl halide being adipoyl chloride.

The halogen used in the halogenation reaction can be chlorine or bromine, with bromine being an especially preferred halogen.

The halogenation reaction of step (a) of the present invention is conducted under conditions wherein a mixture of racemic and meso-dihaloadipoyl halides is formed. Additionally, an acidic compound is formed. The acidic compound formed is a hydrogen halide. For instance if the adipoyl halide is adipoyl chloride and the halogen is bromine, the reaction mixture contains hydrogen bromide.

In the present invention, it has now been surprisingly found that if the acidic compound is not removed, the presence of the acidic compound drives the epimerization of the racemic diester to the meso diester, a reaction to be discussed in more detail below.

In step (b) of the present invention, the resultant mixture of dihaloadipoyl halides of step (a) is esterified. In this step, the reaction mixture also contains a mixture of racemic dialkyl 2,5-dihaloadipate and meso dialkyl 2,5-dihaloadipate and in addition, contains an acidic compound. The esterification reaction is carried out under conventional conditions for such reactions, i.e. using a $C_1$-$C_3$ alcohol at a temperature of about 10° C. to about 25° C. $C_1$-$C_3$ alcohols which can be used in the esterification reaction are methanol and ethanol. If the alcohol used in step (b) is ethanol, then the acidic compound generated is hydrogen chloride.

Since the acidic compounds generated in steps (a) and (b) of the present process have not been removed, they function in the esterification step in a similar manner, that is, the presence of the acidic compounds spontaneously epimerizes the racemic dialkyl 2,5dihaloadipate to the meso diester, as described in step (c) of the present process.

In step (d) of the present process, the meso dialkyl 2,5-dihaloadipate is removed by crystallization, thereby driving the equilibrium of the mixture towards formation of the meso dialkyl ester. Since the removal of the meso dialkyl ester shifts the equilibrium between the racemic dialkyl ester and meso dialkyl ester away from the thermodynamic equilibrium, the epimerization continues in an effort to maintain the thermodynamic equilibrium. Removal of the meso dialkyl ester is accomplished by conventional means, i.e., filtering, washing, etc.

Having described the invention in general terms, reference is now made to specific examples thereof. It is to be understood that these examples are not to be construed as limiting the invention, the scope of which is determined by the appended claims.

Having described the invention in general terms, reference is now made to specific examples thereof. It is to be understood that these examples are not to be construed as limiting the invention, the scope of which is determined by the appended claims.

EXAMPLE 1

Bromination of Adipoyl Chloride

A two liter four neck round bottom flask was assembled on a steam bath. The flask was equipped with a thermometer, paddle-stirrer, dropping funnel and reflux condenser. The top of the reflux condenser was vented into a scrubber system. A sun lamp was positioned two to three inches from the side wall of the flask.

The above described two liter flask was charged with 200 g(1.093 mole) of 98% adipoyl chloride. The sun lamp was turned on and the stirred oil was heated to 75°–85° C. Once at 75°–85° C., 374.3 g(2.342 mole) of liquid bromine was added dropwise over five hours and fifteen minutes. After this addition was complete the reaction was kept at 75°–85° C. for another one hour and forty-five minutes. Thin-layer chromatography at this point indicated incomplete reaction. An additional 78 g (.488 mole) of bromine was added over 45 minutes, followed by 30 minutes of heating at 75° C. to 85° C. Thin-layer chromatography then showed complete reaction. The heating was stopped and the sun lamp was removed. The dropping funnel was replaced with a nitrogen inlet and the condenser was removed. Nitrogen was blown through the flask venting through the scrubber system. It took approximately one hour to purge the bromine color from the flask. The crude oil was used in the following step as is.

EXAMPLE 2

Preparation of Diethyl-meso-dibromoadipate

A two liter three neck round bottom flask was equipped with paddle stirrer and thermometer, then immersed in an ice water bath. The flask was charged with 650 ml 2B ethanol. Crude dibromo adipoyl chloride (1.093 mole) was added to this stirred 2B ethanol, not allowing the internal temperature to exceed 25° C. This addition took forty-five minutes and the resulting suspension was stirred at room temperature for sixteen hours, then at 5° C. for thirty minutes. The suspension was filtered and the moist cake was reslurried briefly in 250 ml fresh 2B ethanol at 10°–15° C. This suspension was filtered and the white solid was washed with a minimal amount of 10°–15° C. 2B ethanol. This first crop was dried at 30° C. in a vacuum oven to yield 205 g(52.1%) of white crystalline solid melting point 64°–66° C.

All the clear yellow ethanol mother liquors from the above were combined and stripped to a 600 ml volume. After standing three days at room temperature, crystals had precipitated from solution. This mixture was stirred for one hour at 5°–10° C., then filtered.

The moist cake was restirred in 150 ml 2B ethanol at 5°–10° C., then filtered and dried at 30° C. in a vacuum oven. This second crop of white crystalline solid weighed 92 g(23.4%) and melted at 64°–66° C.

We claim:

1. A process for the preparation of the meso dialkyl 2,5-dihaloadipate from a mixture of racemic dialkyl 2,5-dihaloadiplate and meso dialkyl 2,5-dihaloadipate comprising
   (a) halogenating an adipoyl halide under conditions wherein a mixture of racemic and meso-dihalo adipoyl halides are formed, said conditions also resulting in the formation of an acidic compound,
   (b) esterifying said mixture of resultant dihalo adipoyl halides under conditions resulting in the formation of a mixture of racemic dialkyl 2,5-dihaloadipate and meso dialkyl 2,5-dihaloadipate, said conditions also resulting in the formation of an acidic compound,
   (c) allowing the mixture of (b) to remain in contact with the acidic compound produced in steps (a) and (b) for a sufficient period of time to allow spontaneous crystallization of said meso ester, said acidic compound epimerizing said racemic ester to said meso ester,
   (d) removing the meso diester thus produced from the equilibrium mixture of (b) by crystallization, whereby said crystallization of the meso diester drives the equilibrium of the mixture towards formation of the meso diester.

2. The process of claim 1 wherein said dialkyl 2,5-dihaloadipate is a $C_1$–$C_3$ ester.

3. The process of claim 2 wherein said dialkyl 2,5-dihaloadipate is the dimethyl ester.

4. The process of claim 2 wherein said dialkyl 2,5-dihaloadipate is the diethyl ester.

5. The process of claim 1 wherein said acidic compound generated in step (a) is hydrogen bromide.

6. The process of claim 1 wherein said acidic compound generated in step (b) is hydrogen chloride.

7. The process of claim 1 wherein said adipoyl halide is adipoyl chloride.

8. The process of claim 1 wherein said dihaloadipate is a dibromoadipate.

9. The process of claim 1 wherein said meso dialkyl 2,5-dihaloadipate is meso diethyl 2,5- dibromoadipate.

* * * * *